US00PP20124P2

(12) United States Plant Patent
van der Spek

(10) Patent No.: US PP20,124 P2
(45) Date of Patent: Jun. 23, 2009

(54) ***HYDRANGEA* PLANT NAMED 'SIDASELI'**

(50) Latin Name: *Hydrangea macrophylla*
Varietal Denomination: Sidaseli

(76) Inventor: Daniel van der Spek, Nieuwkoopseweg 45, 2631 PP Nootdorp (NL)

( * ) Notice: Subject to any disclaimer, the term of this patent is extended or adjusted under 35 U.S.C. 154(b) by 0 days.

(21) Appl. No.: 11/903,264

(22) Filed: Sep. 22, 2007

(51) Int. Cl.
*A01H 5/00* (2006.01)

(52) U.S. Cl. ..... Plt./250

(58) Field of Classification Search ..... Plt./250
See application file for complete search history.

*Primary Examiner*—Annette H Para
*Assistant Examiner*—Loanne C Krawzewicz Myers

(57) ABSTRACT

A new and distinct *Hydrangea* cultivar named 'Sidaseli' is disclosed, characterized by red/purple flowers with a whitish center, slow to moderate growth habit and a compact inflorescence. The new variety is a *Hydrangea* , and naturally blooms from April through September.

1 Drawing Sheet

Latin name of the genus and species: *Hydrangea macrophylla.*
Variety denomination: 'Sidaseli'.

BACKGROUND OF THE INVENTION

The new cultivar is a product of a planned breeding program. The intent of this breeding program was stronger pot plant varieties with attractive flower colors. The new variety was discovered as a seedling within the planned breeding program. This seedling is a result from the crossing of the female parent, an undistributed proprietary variety referred to as 9723 with the male parent, an undistributed proprietary variety referred to as 9654. 'Sidaseli' was selected as a single plant by Daniel van der Spek in May of 1999 in Nootdorp, the Netherlands.

Asexual reproduction of the new cultivar 'Sidaseli' by vegetative cuttings was performed in Nootdorp, the Netherlands and has shown that the unique features of this cultivar are stable and reproduced true to type through 6 successive generations.

SUMMARY OF THE INVENTION

The cultivar 'Sidaseli' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Sidaseli'. These characteristics in combination distinguish 'Sidaseli' as a new and distinct *Hydrangea* cultivar:

1. Flattened inflorescence;
2. Unique petal coloration of red/purple with a white center.
3. Dark foliage;
4. Strong plant, resisting breaking in production and post-harvest situations.

Plants of the new cultivar 'Sidaseli' are similar to plants of the female parent, '9723' in most horticultural characteristics, however, plants of the new cultivar 'Sidaseli' has significantly different flower coloration. Flowers of the new cultivar are distinctively red/purple with a white center, while the female parent has solid red flower coloration and less flowers per inflorescence. 'Sidaseli' differs from the male parent '9654' in foliage color. Foliage of the new cultivar is 139A, much darker than the male parent. Additionally, the new variety has smaller leaves as well as more leaves per lateral branch.

Plants of the new cultivar 'Sidaseli' are similar to plants of the commercial variety 'Twilight,' unpatented in the United States in inflorescence type and color. However, plants of the new cultivar 'Sidaseli' differ in the following characteristics;

1. Foliage of 'Sidaseli' is much darker than 'Twilight'
2. 'Sidaseli' produces more lateral branches than 'Twilight.'
3. 'Sidaseli' flowers earlier than 'Twilight' under natural conditions.
4. 'Sidaseli' flowers earlier than 'Twilight' under production greenhouse conditions.

BRIEF DESCRIPTION OF THE PHOTOGRAPH

The accompanying photograph in FIG. 1 illustrates in full color a typical blooming plant of 'Sidaseli' grown in a greenhouse. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Sidaseli' plants grown in a greenhouse in Brielle, The Netherlands from October 2005 to October 2006. The growing temperature ranged from 16° C. to 17° C. at night to 18° C. to 20° during the day. The pH of the growing medium was between 5.0 and 5.5. 'Sideseli' has has been inserted in its place not been tested for the effect of Aluminum on stem, leaf and flower colors. Measurements and numerical values represent averages of typical flowering types.

Botanical classification: *Hydrangea macrophylla* cultivar 'Sidaseli.'

PROPAGATION

Time to Rooting: 19 to 21 days at approximately 20° C.
Root Description: Fine, fibrous.

PLANT

Growth Habit: Flowering perennial shrub.
Height: Approximately 34 cm to the top of the infloresence.
Blooming period: Naturally blooming April through September.
Plant Spread: Approximately 54.5 cm.
Growth Rate: Moderate.
Branching Characteristics: Moderately free branching.
Length of Lateral Branches: Approximately 24.1 cm.
Number of Lateral Branches: Approximately 16.
Diameter of Lateral Branches: Approximately 0.5 cm.
Pinching Required: Yes.
*Details of pinching.*—The first pinch is given at 8 weeks from the planting of a rooted cutting. A second pinch is given 12 weeks from planting a rooted cutting.
Lateral Branch Shape: Round.
Lateral Branch Texture: Leathery.
Lateral Branch Strength: Very strong.
Lateral Branch Color: Approximately RHS Yellow-Green 144A, slightly tinged at the nodes with RHS Greyed-Purple 183B.
Other Stem or Plant Characteristics: Stems covered with lenticels at a density of approximately 7 lenticels per square cm.
*Lenticel length.*—Approximately 0.2 cm.
*Lenticel width.*—Approximately 0.075 cm.
*Lenticel color.*—About RHS Greyed-Purple 183B.
Number of leaves per lateral branch: Approximately 8.
Age of plant described: Approximately 1 year.

FOLIAGE

Leaf:
*Arrangement.*—Opposite.
*Compound or single.*—Single.
*Average length.*—Approximately 11 cm.
*Average width.*—Approximately 7.1 cm.
*Shape of blade.*—Oval to elliptic oblong.
*Apex.*—Apiculate
*Base.*—Acuminate.
*Attachment.*—Stalked.
*Margin.*—Serrate, approximately 3 teeth per cm.
*Texture of top surface.*—Glossy, non-pubescent.
*Texture of bottom surface.*—Matte, non-pubescent.
*Leaf internode length.*—Approximately 6.5 cm.
*Color.*—Young foliage upper side. Near R.H.S. Green 137A. Young foliage under side. Near R.H.S. Yellow-Green 146B. Mature foliage upper side: Near R.H.S. Green 139A. Mature foliage under side: Near R.H.S. Yellow-Green 146B.
*Venation.*—Type: Pinnate Venation color upper side: Near R.H.S. Yellow-Green 145B. Venation color under side. Near R.H.S. Yellow-Green 145B.
*Durability of foliage to stresses.*—High.

Petiole:
*Average length.*—Approximately 2.1 cm.
*Color.*—Near R.H.S. Yellow-Green 145B, base slightly tinged Greyed-Purple 183D.
*Diameter.*—Approximately 0.3 cm.

FLOWER

Bloom Period:
*Natural season.*—Continuous April through September.
Inflorescence:
*Arrangement.*—Terminal inflorescence.
*Type.*—Compound corymb.
*Height.*—Approximately 6.9 cm.
*Width.*—Approximately 15.2 cm.
*Quantity of flowers per inflorescence.*—Fertile flowers, approximately 200. Sterile Flowers (described as bracts), approximately 9.
Bud:
*Bud shape* (*sterile flowers*).—Obovate.
*Bud length* (*sterile flowers*).—Approximately 0.55 cm.
*Bud diameter* (*sterile flowers*).—Approximately 0.3 cm.
*Bud color* (*sterile flowers*).—Near R.H.S. Red-Purple 57C. Base/calyx: Near R.H.S. Yellow-Green 144C.
*Bud shape* (*fertile flowers*).—Globose.
*Bud length* (*fertile flowers*).—Approximately 0.4 cm.
*Bud diameter* (*fertile flower*).—Approximately 0.4 cm.
*Bud color* (*fertile flowers*).—Base Yellow-Green 146C, tip Red-Purple 60C.
Flower:
*Shape.*—Rotate.
*Facing direction.*—Sterile flowers facing out, fertile flowers facing all directions.
*Quantity of flowers per lateral stem.*—209.
*Quantity of flowers and buds per plant.*—Approximately 3350.
*Diameter of entire flower.*—Fertile; Approximately 0.8 cm. Sterile: Approximately 5.7 cm.
*Depth of flower.*—Fertile; Approximately 0.6 cm. Sterile: Approximately 2 cm.
*Rate of opening.*—Individual flowers: Fully open approximately 5 days from the bud stage. Whole Plant: Approximately 50% of flowers open at once.
*Flower longevity on plant.*—Fertile flowers: Approximately 5 days. Sterile flowers: Approximately 25 days.
*Persistent of self-cleaning.*—Persistent.
*Fragrance.*—No.
Petals:
*Length of petal.*—Approximately 0.45 cm.
*Width of petal.*—Approximately 0.25 cm.
*Apex.*—Acute.
*Base.*—Cordate.
*Shape of petal.*—Ovate.
*Petal margin.*—Entire.
*Petal arrangement.*—Rotate.
*Petal number.*—Approximately 5.
*Petal fused.*—No.
*Petal appearance.*—Dull.
*Petal texture* (*both surfaces*).—Smooth.
Color:
*Upper surface at first opening.*—Near Red-Purple 57D. Base: Slightly Near White 155 with Red-Purple 57D.

*Upper surface at maturity.*—Near Red-Purple 58B. Base: Near White 155 AND Green-Yellow 1D with Near Red-Purple 58B.
*Upper surface at fading.*—Near Red-Purple 57C. Base: Near White 155 with Near Red-Purple 57D.
*Under surface at first opening.*—Near Red-Purple 57C.
*Under surface at maturity.*—Near Red-Purple 59C. Base: Near Red-Purple 59D.
*Under surface at fading.*—Near Red-Purple 59C. Base: Near Red-Purple 59D.

Petaloids: No.
Fragrance: None.

CALYX

Present: Yes.
Shape: Rotate, lower ¾ fused.
Length: Approximately 0.35 cm.
Diameter: Approximately 0.4 cm.

SEPAL

Sepals: Only sterile flowers have sepals.
Number: Average 5.
Sepal Appearance: Smooth.
Sepal Arrangement: Rotate.
Sepal length: Approximately 0.35 cm.
Sepal width: Approximately 0.1 cm.
Sepal shape: Deltoid.
Apex shape: Acute.
Base: Fused into a tube ⅔ of length.
Margin: Entire.
Texture (both surfaces): Smooth.
Color: Upper side near R.H.S. Yellow-Green 144C. Under side near R.H.S. Yellow-Green 144C.

PEDUNCLE

Length: Approximately 3.9 cm.
Diameter: Approximately 0.3 cm.
Angle: Approximately 35 degrees (0 degrees=straight upright).
Strength: Strong.
Color: Near R.H.S. Yellow-Green 144C.

PEDICEL

Present: Yes.
Length (sterile flowers): Approximately 0.3 cm.
Diameter (sterile flowers): Approximately 0.5 cm.
Angle (sterile flowers): Approximately 10 degrees.
Strength (sterile flowers): Moderate.
Color (sterile flowers): Near Yellow-Green 144C, slightly tinged base near Red-Purple 57D.
Length (fertile flowers): Approximately 0.08 cm.
Diameter (fertile flowers): Approximately 0.03 cm.
Angle (fertile flowers): Approximately 5 degrees.
Strength (fertile flowers): Moderate.
Color (fertile flowers): Near Yellow-Green 144C.

REPRODUCTIVE ORGANS

*Number of pistils per flower.*—3.
*Pistil length.*—Approximately 0.2 cm.
*Stigma shape.*—Lobed.
*Stigma color.*—Near Red-Purple 57D.
*Style color.*—Near Red-Purple 62D.
*Style length.*—Approximately 0.1 cm.
*Ovary color.*—Near Yellow-Green 154C.
*Stamens.*—Average 10.
*Anther shape.*—Broad kidney-shaped.
*Anther size.*—1 cm.
*Anther color.*—Near White 155A, filament colored Red-Purple 62B.
*Pollen color.*—Near White 155A.
*Pollen quantity.*—Very low.

OTHER CHARACTERISTICS

Disease Resistance: Neither resistance nor susceptibility to diseases or pests has been observed in this variety.
Drought Tolerance and Cold Tolerance: Semi-hardy perennial, tolerant of some high temperatures. Upper limit of temperature tolerance has not been observed, however, known to tolerate temperatures of at least up to 40° C. Lower limits have also not been observed, however, observed hardy to −15° C. No drought tolerance has been observed.
Fruit/seed production: No fruits/seeds detected to date.
Effect of aluminum added to the growing medium: 'Sidaseli' has not been tested for the effect of Aluminum on stem, leaf and flower colors.

What is claimed is:

1. A new and distinct cultivar of *Hydrangea* plant named 'Sidaseli' as herein illustrated and described.

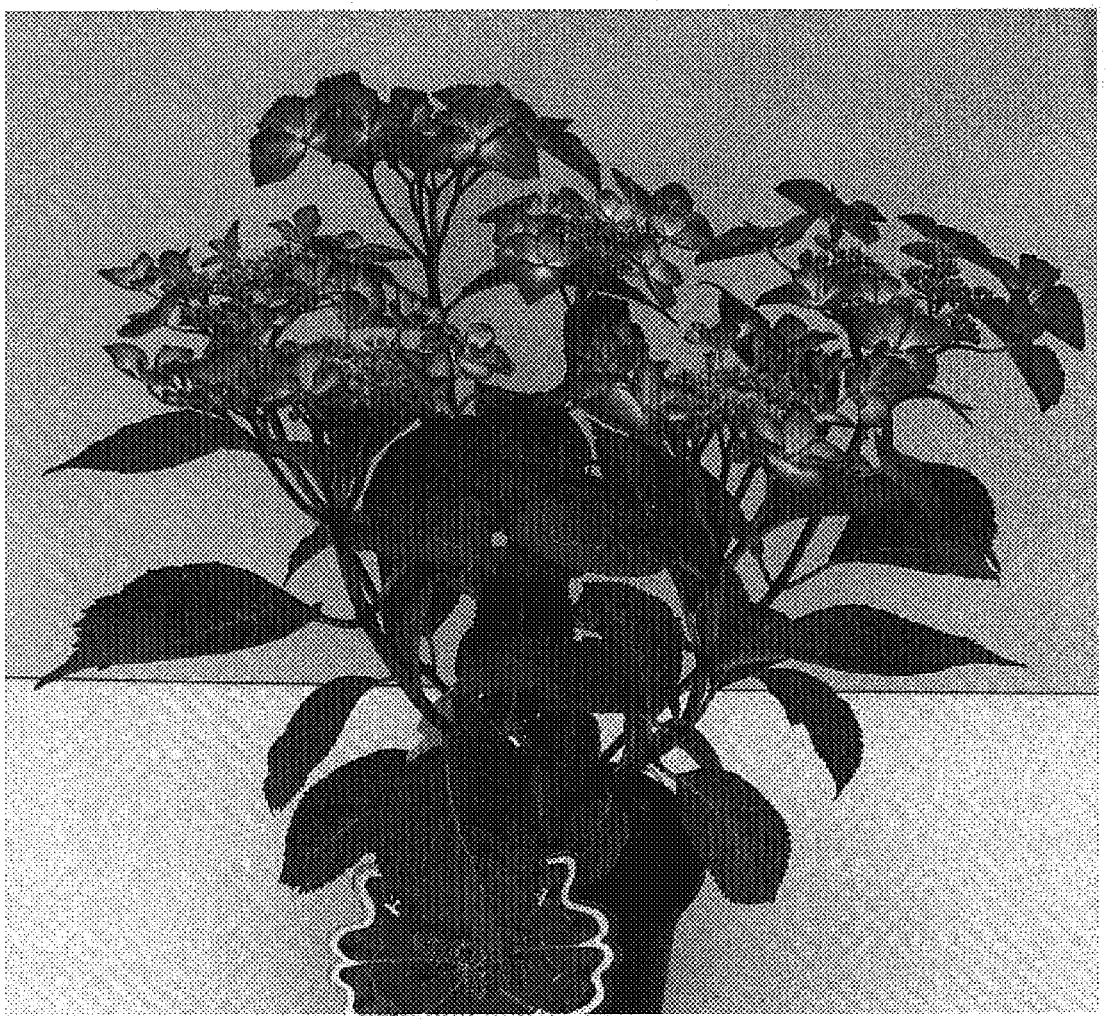

* * * * *